US006471970B1

(12) United States Patent
Fanara et al.

(10) Patent No.: US 6,471,970 B1
(45) Date of Patent: Oct. 29, 2002

(54) USE OF PHARMACEUTICAL COMPOSITIONS CAPABLE OF BEING GELLED IN PERIODONTOLOGY

(75) Inventors: Domenico Fanara, Wanze (BE); Henri Vranckx, Brussels (BE); Michel Deleers, Linkebeek (BE); Pierre Grognet, Brussels (BE)

(73) Assignee: UCB, S.A., Brussels (BE)

( * ) Notice: Subject to any disclaimer, the term of this patent is extended or adjusted under 35 U.S.C. 154(b) by 43 days.

(21) Appl. No.: 09/674,163

(22) PCT Filed: Apr. 16, 2000

(86) PCT No.: PCT/EP99/02552

§ 371 (c)(1),
(2), (4) Date: Oct. 27, 2000

(87) PCT Pub. No.: WO99/56726

PCT Pub. Date: Nov. 11, 1999

(30) Foreign Application Priority Data

Apr. 30, 1998 (BE) .............................................. 9800329

(51) Int. Cl.⁷ .......................... A61K 9/10; A61K 47/12; A61K 47/24; A61K 6/00
(52) U.S. Cl. ...................... 424/400; 424/422; 424/425; 424/484; 514/2; 514/784; 514/786; 514/944; 514/900
(58) Field of Search ................................ 424/400, 405, 424/435, 484, 422, 423, 424, 425, 426; 514/2, 152, 181, 398, 626, 635, 784, 785, 786, 787, 788, 900, 902, 944

(56) References Cited

U.S. PATENT DOCUMENTS

| 5,230,895 A | * | 7/1993 | Czarnecki et al. | ........... 424/422 |
| 5,230,899 A | * | 7/1993 | Park et al. | ................... 424/450 |
| 5,958,379 A | * | 9/1999 | Regenold et al. | .............. 424/47 |
| 6,117,864 A | * | 9/2000 | Morita et al. | ................ 514/212 |
| 6,210,743 B1 | * | 4/2001 | Clapp et al. | ................. 426/662 |

FOREIGN PATENT DOCUMENTS

| EP | 0 429 224 | 5/1991 |
| EP | 0 550 960 | 7/1993 |
| WO | 94/10978 | 5/1994 |
| WO | 95/03787 | 2/1995 |
| WO | 97/15285 | 5/1997 |

OTHER PUBLICATIONS

Budavari et al, eds. The Merck Index, 11$^{th}$ ed. Rahway: Merck & Co., Inc. p. 311, 1989.*

* cited by examiner

Primary Examiner—Jeffrey E. Russel
(74) Attorney, Agent, or Firm—Wenderoth, Lind & Ponack, L.L.P.

(57) ABSTRACT

A method is described for preparing a fluid pharmaceutical composition which allows the controlled release of at least one active substance. The method involves mixing a therapeutically effective amount of at least one active substance, from 3 to 55% by weight of phospholipid, from 16 to 72% by weight of pharmaceutically acceptable solvent, and from 4 to 52 % by weight of fatty acid. The composition has a property of gelling instantaneously in the presence of an aqueous phase.

14 Claims, No Drawings

USE OF PHARMACEUTICAL COMPOSITIONS CAPABLE OF BEING GELLED IN PERIODONTOLOGY

This application is a 371 of PCT/EP99/02552 filed Apr. 16, 2000.

The present invention relates to pharmaceutical compositions which allow the sustained release of at least one active substance, to methods for preparing these compositions, as well as to their use for treating periodontitis, gingivitis, dental abscesses, mouth ulcers and mycoses.

Periodontitis is a disease which is revealed by the destruction of the supporting tissues of teeth subsequent to an inflammation which is caused by the anaerobic microorganisms of dental plaque. Without treatment, the disease inevitably develops and increasing numbers of bacterial populations continuously maintain the immune reaction which triggers the phenomena of periodontal disease and periodontoclasia. As soon as it reaches a depth greater than 3 mm, the gingivo-dental crevice is considered to be a periodontal pocket. Periodontitis is also accompanied by the resorption of the alveolar bone. Its development finally leads to tooth loss.

Periodontitis is a disease which more greatly affects the adult population over forty years old. Periodontitis is not, however, a disease of elderly people; it quite frequently affects even the young.

It is possible to distinguish acute infections (superficial gingivitis or deep periodontal abscesses); "rapidly evolving" infections (adolescent and young-adult periodontitis); and finally, chronic infections which evolve in stages (chronic periodontal disease).

The methods for treating periodontitis comprise in particular daily hygiene and mechanical means (cleaning, descaling, surfacing of roots, etc.), as well as local and systemic antiseptic and antibiotic means.

Antiseptics can be administered locally in the form of mouthwashes, toothpastes or creams. However, this mode of local administration does not allow the antiseptics to diffuse all the way to the bottom of the periodontal pockets. The function of this mode of administration cannot go beyond the stage of prophylaxis.

With regard to antibiotics, they are no more active by topical administration for the same reason, since they do not manage to reach the depth of the bacterial biofilms (or plaque). When the severity of the case makes it necessary, antibiotics are thus generally administered systemically, relying on their diffusion as far as the periodontal pockets through the gingival fluid which continually flows into them.

Another method consists in using pharmaceutical compositions which allow the controlled release of antiseptic or antibiotic agents, and which are inserted directly at the bottom of the periodontal pocket. Sustained-release compositions exist which are deposited on solid devices such as soaked threads, gelatin chips, etc. Such devices can leave insoluble frameworks in place which must, of course, be removed at the end of treatment.

The literature also mentions fluid pharmaceutical compositions, such as more or less viscous emulsions or suspensions, which are administered into the periodontal pocket generally with the aid of syringes.

International patent application WO 95/34287 describes biodegradable lipid compositions in the form of L2 crystalline phases which allow the controlled release of active substances and which comprise, besides the active substance, at least one unsaturated fatty acid diacylglycerol which has 16 to 22 carbon atoms or saturated fatty acid diacylglycerol which has 14 to 22 carbon atoms, at least one phospholipid chosen from glycerophosphatides and sphingophosphatides, and, optionally, at least one polar liquid chosen from water, glycerol, ethylene glycol and propylene glycol. These compositions have the characteristic of transforming into cubic liquid crystal phases upon contact with water, which makes it possible to "mould" the active substance in the site where it is desired for the action to take place. The said document mentions, among other uses, the possibility of using such compositions for treating periodontitis. However, the effectiveness of such compositions in the treatment of periodontitis is not illustrated in that document.

European patent 429224 describes compositions which are in the form of gels containing from 1 to 99% by weight of monoolein and from 1 to 90% by weight of active substance, which are placed in the periodontal cavity. In the presence of the surrounding water, these compositions become more viscous and keep the active substance close to its site of action. The active substance is released slowly in controlled fashion.

U.S. Pat. No. 5,230,895 describes the use of compositions which are in the form of solutions or pastes which are capable of transforming into gel when they have been placed in the periodontal pocket. These compositions are biodegradable and allow the controlled release of the active substance in the site of action. They contain a mixture of glycerides and of an active substance chosen such that it is capable of forming a gel in the environment of the periodontal pocket. The compositions illustrated in the said document contain at least 70% of Myverol™ 18–92, which is a composition of sunflower monoglycerides which has a monoglyceride content of at least 90%.

U.S. Pat. No. 5,143,934 describes compositions which allow the administration, by controlled release, of an active substance in a periodontal pocket, and which comprise at least one monoglyceride and at least one plant oil in proportions which are sufficient to form a liquid crystal phase upon contact with the water present in the periodontal pocket. These compositions are solid at room temperature, but they have a melting point which is lower than body temperature.

In that document, the results obtained for several compositions of this type are compared with the results obtained with a conventional mechanical treatment. It is noted that the compositions which are described therein make it possible to obtain a reduction in the size of the periodontal pockets and a decrease in bleeding during three months of treatment. However, the effect obtained by applying the compositions is no better, and is even slightly worse, than the result which may be obtained with the reference mechanical treatment.

In addition, since the compositions described in U.S. Pat. No. 5,143,934 are solid at room temperature, they must be liquefied at the moment of insertion into the periodontal pocket.

The applicant has now just discovered novel pharmaceutical compositions which can be easily applied into the periodontal pocket and which allow the sustained release of active substances in this pocket. The applicant has in particular just discovered that these novel compositions are very well suited to the treatment of periodontitis, due to both their effectiveness and their ease of use. In addition, these compositions are obtained by an extremely simple preparation method.

Consequently, the present invention relates to fluid pharmaceutical compositions which allow the controlled release of at least one active substance and which comprise a) a therapeutically effective amount of at least one active substance,
b) from 3 to 55% by weight of phospholipid,
c) from 16 to 72% by weight of pharmaceutically acceptable solvent, and
d) from 4 to 52% by weight of fatty acid, these compositions having the property of gelling instantaneously in the presence of an aqueous phase.

According to another aspect, the invention relates to methods for preparing these compositions.

According to a third aspect, the invention relates to the use of these compositions for treating periodontitis, gingivitis, dental abscesses, mouth ulcers and mycoses.

The compositions according to the present invention comprise a therapeutically effective amount of at least one active substance. The latter can be lipid-soluble or water-soluble. By way of example, mention will be made of antibiotics, in particular antibiotics which are active against anaerobic bacteria, such as doxycycline or minocycline, and the pharmaceutically acceptable salts thereof, anti-infectious agents such as metronidazole, chlorhexidine, benzalkonium chloride, p-chloro-m-cresol, 2,4-dichlorobenzyl alcohol, hexamidine or chlorofen, and the pharmaceutically acceptable salts thereof, local anesthetics such as lidocaine, procaine, tetracaine, articaine, bupivacaine, mepivacaine or prilocaine, and the pharmaceutically acceptable salts thereof, steroidal or other anti-inflammatory agents such as hydrocortisone, cortisone, prednisone, prednisolone, methylprednisolone, triamcinolone, betamethasone or dexamethasone, and the pharmaceutically acceptable salts thereof, as well as aceclofenac, diclofenac, ibuprofen and piroxicam, and the pharmaceutically acceptable salts thereof, anti-mycotic agents such as griseofulvin, amphotericin B, natamycin or nystatin, and the pharmaceutically acceptable salts thereof, or alternatively peptide active substances such as calcitonin, somatostatin, bone growth hormone and other growth or repair factors.

The compositions according to the present invention contain from 3 to 55% of phospholipid. The phospholipids which can be used according to the present invention are phosphoric esters of polyols and of fatty acids. They may originate from very varied sources, both natural and via a synthetic pathway. The phospholipids may be hydrogenated or nonhydrogenated. By way of examples, mention will be made of phosphatidylchloine, hydrogenated phosphatidylcholine, phosphatidylglycerol salts, diccaproylphosphatidylcholine or distearoylphosphatidylglycerol salts. These phospholipids can also be used as a mixture. Preferably, the phospholipid which is present in the compositions according to the present invention is phosphatidylcholine.

When the phospholipid is chosen from phosphatidylcholine, phosphatidylglycerol salts, dicaproylphosphatidylcholine or distearoylphosphatidylglycerol salts, the preferred compositions according to the present invention contain from 15 to 55% by weight of phospholipid. When the phospholipid is a hydrogenated phosphatidylcholine, the compositions according to the present invention contain from 3 to 11%, preferably from 3 to 10%, by weight of phospholipid.

The compositions according to the present invention contain one or more pharmaceutically acceptable solvents. The expression "pharmaceutically acceptable solvent" is intended to mean a solvent such as propylene glycol, polyethylene glycols, mineral oils, such as liquid paraffin or silicone oils, or any other solvent in which the phospholipid used is soluble. Mixtures of several pharmaceutically acceptable solvents can also be used. Propylene glycol is preferably used. The solvent used is pharmaceutically acceptable, which means that the solvent will not produce any biological reaction reflected by infections, inflammations or other phenomena of rejection.

The compositions according to the present invention also contain from 4 to 52% of at least one fatty acid. The fatty acids which can be used according to the present invention are saturated or unsaturated organic carboxylic acids containing from 4 to 22 carbon atoms, preferably from 8 to 18 carbon atoms. By way of example, mention will be made of oleic acid, caprylic acid, capric acid, caproic acid, myristic acid, butyric acid, etc. Mixtures of fatty acids can also be used. The preferred fatty acid according to the present invention is oleic acid.

Optionally, the compositions according to the present invention can also contain up to 15% by weight of water. It will be noted that the amount of water which is present in the compositions according to the invention is chosen such that the composition has the desired consistency for the use envisaged.

The applicant has also discovered that phospholipids which are in the form of commercially available mixtures are suitable for the compositions according to the present invention. As examples of such commercially available compositions, mention will be made of Phosal 50 PG™ (55.8% of phosphatidylcholine, 1.9% of soybean fatty acids, 2.9% of sunflower monoglycerides, 1.9% of ethanol, 37.3% of propylene glycol and 0.2% of ascorbyl palmitate) and Phosal 53 MCT™ (60.8% of phosphatidylcholine, 2% oleic acid, 3% of sunflower monoglycerides, 5% of ethanol, 29% of triglycerides and 0.2% of ascorbyl palmitate), which are available from Nattermann Phospholipid GmbH.

The compositions according to the present invention can also contain the following optional components: up to 5% by weight of monoglyceride or of diglyceride or of a mixture of mono- and of diglyceride, and/or up to 15% by weight of triglycerides.

The compositions according to the present invention can also contain one or more preservatives (such as ethanol), one or more antioxidants (such as ascorbyl palmitate) or one or more complexing agents (such as EDTA (ethylenediaminetetraacetate)).

The compositions according to the present invention allow the controlled release of at least one active substance. The term "controlled release" is intended to mean an active substance release profile which is desirable for the treatment envisaged. The release of the active substance can thus be more or less held back or slowed down as a function of the active substance used and of the desired therapeutic effect. It will be noted that the release of the active substance can be easily controlled by simple variations in the proportions of the components of the compositions according to the present invention. The compositions are thus very well suited to diverse therapeutic applications in which the controlled release of an active substance is sought in a very precise biological site.

The compositions according to the present invention are fluid pharmaceutical compositions which are in the form of emulsions, suspensions or oily preparations. They have the property of gelling instantaneously in the presence of an aqueous phase. Specifically, when the compositions according to the present invention are placed in the presence of an excess of aqueous phase, they go from a fluid state to the state of a gel which is immiscible with the surrounding aqueous phase.

This makes the compositions of the invention particularly suitable for treating diverse conditions requiring a local treatment in the medium which is permanently irritated with an aqueous phase. Such uses include in particular the treatment of periodontitis, gingivitis or dental abscesses, or alternatively the treatment of mouth ulcers and mycoses.

The preparations according to the invention can also be judiciously used to obtain, via the subcutaneous and intramuscular routes, sustained and programmed release of certain medicinal products. Upon contact with water, a gel forms under skin or in the muscle, and the medicinal product may diffuse and be released slowly from this gel.

Consequently, the present invention also relates to the use of compositions according to the present invention for treating a person or an animal suffering from periodontitis, gingivitis or dental abscesses, mouth ulcers or mycoses, characterized in that a composition according to the present invention is applied to the site requiring the treatment.

In the case of a patient suffering from periodontitis, the treatment method consists in applying the composition of the invention into one or more periodontal pockets by means of a dental instrument which is suitable for this purpose. Application by means of syringes is particularly easy and makes it possible to obtain an extremely satisfactory result.

In the case of a patient suffering from gingivitis, dental abscesses, mouth ulcers or mycoses, the treatment consists of a simple application of the composition to the site requiring treatment. Optionally, this application can be carried out by the patient himself.

According to another aspect, the present invention relates to methods for preparing compositions according to the present invention. The compositions according to the present invention are obtained by a method comprising the following successive steps:

i) the phospholipid(s) is(are) dissolved in the pharmaceutically acceptable solvent(s);

ii) the fatty acid(s) is(are) added to the phospholipid solution with stirring;

iii) the active substance(s) is(are) incorporated into the mixture obtained at the end of step ii), and iv) water is optionally added to the composition obtained in step iii).

When the active substance is water-soluble, it is dissolved in a minimal amount of water before the incorporation in step iii). When the active substance is not soluble in water, it is incorporated in step iii) in the mixture of phospholipid, pharmaceutically acceptable solvent and fatty acid. In the case of substance which is both insoluble in water and insoluble or relatively insoluble in lipid, it is also incorporated in step iii), optionally in micronized form.

The following examples illustrate the present invention without, however, limiting it. In these examples, all the parts are expressed by weight. The following commercially available products were obtained from Nattermann Phospholipid GmbH and have the following compositions (percentages by weight):

Phospholipon 90™: phosphatidylcholine;

Phosal 50 PG™: 55.8% of phosphatidylcholine, 1.9% of soybean fatty acids, 2.9% of sunflower monoglycerides, 1.9% of ethanol, 37.3% of propylene glycol and 0.2% of ascorbyl palmitate;

NAT 8449™: 60% of phosphatidylcholine and 40% of propylene glycol

Phosal 53 MCT™: 60.8% of phosphatidylcholine, 2% of oleic acid, 3% of sunflower monoglycerides, 5% of ethanol, 29% of triglycerides and 0.2% of ascorbyl palmitate;

Phospholipon G-Na™: sodium salt of 3(3-sn-phosphatidyl)glycerol from soybean;

Phospholipon CC™: 1,2-dicaproyl-sn-glycero(3) phosphocholine;

Phospholipon SG-Na™: sodium salt of 1,2-distearoyl-sn-glycero(3)phosphoglycerol;

Phospholipon 90 H™: hydrogenated soybean (3-sn-phosphatidyl)choline.

EXAMPLE 1

This example illustrates the preparation of diverse compositions according to the invention. The compositions described below are in the form of more or less viscous emulsions, suspensions or solutions which gel instantaneously in the presence an aqueous phase.

General Procedure A:

Phosal 50 PG™ or NAT 8449™ and oleic acid are mixed with stirring. The active substance is introduced into the mixture with stirring. After homogenization, water is optionally added to make the preparation more viscous.

General Procedure B:

Phospal 50 PG™ or NAT 8449™ and oleic acid are mixed with stirring. The active substance is dissolved in water, and the solution thus obtained is introduced into the Phosal 50 PG™ or NAT 8449™/oleic acid mixture with stirring.

1.1. Preparation with Metronidazole Benzoate

The preparations which have the compositions presented in Table 1 are obtained according to general procedure A.

TABLE 1

| Metronidazole Compositions A and B (parts) | | | | | |
|---|---|---|---|---|---|
| Composition | $A_1$ | $A_2$ | $A_3$ | $B_1$ | $B_2$ |
| Phosal 50 PG ™ | 54.6 | 77.4 | 81.9 | — | — |
| NAT 8449 ™ | — | — | — | 72.8 | 45.5 |
| Oleic acid | 36.4 | 13.6 | 9.1 | 18.2 | 45.5 |
| Metrodinazole benzoate | 5.0 | 5.0 | 5.0 | 5.0 | 5.0 |
| Water | 4.0 | 4.0 | 4.0 | 4.0 | 4.0 |

1.2 Preparation with Chlorhexidine Diacetate

The preparations which have the compositions presented in Table 2 are obtained according to general procedure A.

TABLE 2

| Chlorhexidine Compositions C and D (parts) | | | | |
|---|---|---|---|---|
| Composition | $C_1$ | $C_2$ | $D_1$ | $D_2$ |
| Phosal 50 PG ™ | 51.0 | 63.8 | — | — |
| NAT 8449 ™ | — | — | 59.5 | 51.0 |
| Oleic acid | 34.0 | 21.2 | 25.5 | 34.0 |
| Chlorhexidine diacetate | 15.0 | 15.0 | 15.0 | 15.0 |

1.3. Preparation with Doxycycline Hyclate.

The preparations which have the compositions presented in Table 3 are obtained according to general procedure b.

TABLE 3

Doxycycline Compositions E and F (parts)

| Composition | $E_1$ | $E_2$ | $F_1$ | $F_2$ |
|---|---|---|---|---|
| Phosal 50 PG ™ | 43.0 | 64.5 | — | — |
| NAT 8449 ™ | — | — | 51.6 | 34.4 |
| Oleic acid | 43.0 | 21.5 | 34.4 | 51.6 |
| Doxycycline hyclate | 5.0 | 5.0 | 5.0 | 5.0 |
| Water | 9.0 | 9.0 | 9.0 | 9.0 |

1.4. Preparation with Minocycline Hydrochloride.

The preparations which have been compositions presented in Table 4 are obtained according to general procedure A.

TABLE 4

Minocycline Compositions G and H (parts)

| Composition | $G_1$ | $G_2$ | $H_1$ | $H_2$ |
|---|---|---|---|---|
| Phosal 50 PG ™ | 45.5 | 77.4 | — | — |
| NAT 8449 ™ | — | — | 68.3 | 45.5 |
| Oleic acid | 45.5 | 13.6 | 22.7 | 45.5 |
| Minocycline hydrochloride | 5.0 | 5.0 | 5.0 | 5.0 |
| Water | 4.0 | 4.0 | 4.0 | 4.0 |

1.5. Preparation with 2,4-Dichlorobenzyl Alcohol

The preparations which have the compositions presented in Table 5 are obtained according to general procedure A.

TABLE 5

2,4-Dichlorobenzyl alcohol Compositions I and J (parts)

| Composition | I | J |
|---|---|---|
| Phosal 50 PG ™ | 80 | — |
| NAT 8449 ™ | — | 80 |
| Oleic acid | 19 | 19 |
| 2,4-Dichlorobenzyl alcohol | 1 | 1 |

1.6. Preparation with Hydrocortisone Succinate

The preparations which have the compositions presented in Table 6 are obtained according to general procedure B.

TABLE 6

Hydrocortisone Compositions K and L (parts)

| Composition | K | L |
|---|---|---|
| Phosal 50 PG ™ | 80 | — |
| NAT 8449 ™ | — | 67.0 |
| Oleic acid | 15 | 28.0 |
| Hydrocortisone succinate | 1 | 1 |
| Water | 4 | 4 |

1.7. Preparation with Lidocaine Hydrochloride

The preparations which have the compositions presented in Table 7 are obtained according to general procedure B.

TABLE 7

Lidocaine Compositions M and N (parts)

| Composition | M | N |
|---|---|---|
| Phosal 50 PG ™ | 80 | — |
| NAT 8449 ™ | — | 66 |
| Oleic acid | 14 | 28 |
| Lidocaine hydrochloride | 2 | 2 |
| Water | 4 | 4 |

EXAMPLE 2

Release Tests

Preparations $A_2$ and $B_1$ prepared in Example 1 were subjected to a release test carried out according to the standards in the 23rd edition of the U.S. pharmacopea (USP 23), using the machine No. 1 at a temperature of 37° C., with the paddles rotating at 50 rpm.

This test showed that preparation $A_2$ releases approximately 60% of the active principle in 6 hours, the release then continuing slowly to reach approximately 65% in 24 hours. With regard to preparation $B_1$, it releases approximately 45% of the active principle in 6 hours, and then the release continues slowly to reach approximately 55% in 24 hours.

EXAMPLE 3

This example shows that various pharmaceutically acceptable salts can be used in the compositions according to the present invention.

3.1. Composition O

Phospholipon 90™ (30 parts by weight) is dissolved while hot in polyethylene glycol 400 (45 parts by weight). After cooling, oleic acid is added with stirring. Upon contact with an aqueous solution, the preparation gels instantaneously.

This example shows that propylene glycol can be replaced with PEG 400.

3.2. Compositions P 40.9 parts of NAT 8449™, 27.3 parts of PEG 400 and 22.8 parts by weight of oleic acid are mixed with stirring. Water (9 parts by weight) is added with stirring in order to make the preparation more viscous.

The preparations which have the compositions presented in Table 8 are obtained according to this procedure.

TABLE 8

Compositions P (parts)

| Composition | $P_1$ | $P_2$ | $P_3$ |
|---|---|---|---|
| NAT 8449 ™ | 34.1 | 40.9 | 61.4 |
| PEG 400 | 34.1 | 27.3 | 6.8 |
| Oleic acid | 22.8 | 22.8 | 22.8 |
| Water | 9.0 | 9.0 | 9.0 |

EXAMPLE 4

This example shows that the compositions according to the present invention can also contain triglycerides.

Composition Q 61.2 parts of Phosal 50 PG™, 20.4 parts of Phosal 53 MCT™ and 14.4 parts of oleic acid are mixed with stirring. 4 parts of water are then added to this mixture with stirring.

This preparation gels instantaneously upon contact with an aqueous phase.

EXAMPLE 5

This examples shows that the compositions according to the present invention can contain various types of phospholipid. The phospholipids used are the sodium salt of 3-(3-sn-phosphatidyl)glycerol from soybean (Phospholipon G-Na™), 1,2-dicaproyl-sn-glycero(3)phosphocholine (Phospholipon CC™), the sodium salt of 1,2-distearoyl-sn-glycero(3)phosphoglycerol (Phospholipon SG-Na™) and hydrogenated soybean (3-sn-phosphatidyl)choline (Phospholipon 90H™).

The compositions P presented in Table 9 are obtained by mixing the various components with stirring. These four compositions gel instantaneously in the presence of an aqueous phase.

TABLE 9

| Composition | Compositions R (parts) | | | |
|---|---|---|---|---|
|  | $R_1$ | $R_2$ | $R_3$ | $R_4$ |
| Phospholipon G-Na ™ | 30 | — | — | — |
| Phospholipon CC ™ | — | 30 | — | — |
| Phospholipon SG-Na ™ | — | — | 15 | — |
| Phospholipon 90H ™ | — | — | — | 3 |
| PEG 400 | 45 | 45 | 60 | 72 |
| Oleic acid | 25 | 25 | 25 | 25 |

EXAMPLE 6

This examples shows that oleic acid can be replaced with other fatty acids or with a fatty alcohol in the compositions according to the present invention.

The Compositions S presented in Table 10 are obtained by mixing the various components with stirring. These four compositions gel instantaneously in the presence of an aqueous phase.

TABLE 10

| Composition | Compositions S (parts) | | | |
|---|---|---|---|---|
|  | $S_1$ | $S_2$ | $S_3$ | $S_4$ |
| Phosal 50PG ™ | 80 | 80 | 80 | 80 |
| Caprylic acid | 20 | — | — | — |
| Capric acid | — | 20 | — | — |
| Oleic acid | — | — | 20 | — |
| Oleyl alcohol | — | — | — | 20 |

EXAMPLE 7

Measurement of the rate of release as a function of the excipients.

7.1.

The Compositions T presented in Table 10 are obtained by adding the desired amount of an aqueous solution containing 10% of Sicomet-FDC blue 1 dye to the mixture of the other components, with stirring. Compositions $T_1$ to $T_6$ gel instantaneously in the presence of an aqueous phase.

TABLE 11

| Composition | Compositions T (parts) | | | | | | |
|---|---|---|---|---|---|---|---|
|  | Control | $T_1$ | $T_2$ | $T_3$ | $T_4$ | $T_5$ | $T_6$ |
| Phosal 50PG ™ | — | 81.6 | 68.3 | 68.3 | 68.3 | 68.3 | 68.3 |
| Oleic acid | — | 14.4 | 22.7 | 18.2 | 13.7 | 18.2 | 9.0 |
| Miglyol 810N ™ | — | — | — | 4.5 | 9.0 | — | 13.7 |
| Phosal 53 MCT ™ | — | — | — | — | — | 4.5 | — |
| Dye solution | 100 | 4.0 | 9.0 | 9.0 | 9.0 | 9.0 | 9.0 |

The release test is carried out as follows. Equal amounts of preparations $T_1$ to $T_6$ and of the control solution are placed in a well which is hollowed out at the center of a layer of trypticase soy agar which has a constant thickness and which has been poured in a Petri dish. The rate of diffusion of the dye is determined by measuring the diameter of the dye stain as a function of time. The results obtained for the control solution and the solutions $T_1$ to $T_6$ are in Table 12.

TABLE 12

| Time | Rate of release of preparations $T_1$ to $T_6$. | | | | | | |
|---|---|---|---|---|---|---|---|
|  | Diameter of the stain in mm. | | | | | | |
| (hours) | Control | $T_1$ | $T_2$ | $T_3$ | $T_4$ | $T_5$ | $T_6$ |
| 0 | 16.97 | 18.74 | 18.61 | 17.66 | 18.36 | 18.49 | * |
| 3 | 49.55 | — | — | — | — | — | * |
| 6 | 62.18 | 29.56 | 29.14 | 28.58 | 23.12 | 33.33 | * |
| 24 | 90.10 | 51.00 | 30.38 | 30.57 | 24.59 | 52.96 | * |
| 36 | 96.29 | 57.45 | 34.02 | 33.67 | 31.23 | 54.55 | * |
| 72 | 108.52 | 60.45 | 39.29 | 34.58 | 31.82 | 68.67 | * |

*No diffusion is observed.

This example shows that the rate of release of an active substance can be controlled through the choice of the components of the preparation.

7.2.

Similarly, the Compositions U given in Table 13 were prepared, and it was noted that the diffusion of the dye decreases with the oleic acid content.

TABLE 13

| Composition | Compositions U (parts) | | |
|---|---|---|---|
|  | $U_1$ | $U_2$ | $U_3$ |
| Phosal 50PG ™ | 81.6 | 86.4 | 91.2 |
| Oleic acid | 14.4 | 9.6 | 4.8 |
| Dye solution | 4.0 | 4.0 | 4.0 |

EXAMPLE 8

Clinical Trial

The effectiveness of the compositions according to the present invention in treating periodontitis was evaluated in a clinical trial in which preparation $A_2$ containing 5% of metronidazole benzoate was injected into the periodontal pockets of patients suffering from periodontitis.

The test comprised two parts: a study directed toward measuring the rate of diffusion of the benzoic acid and of the metronidazole in the gingival fluid and a medical study directed toward evaluating the recovery progress of patients over the course of time.

Just before the start of the trial, the supra-gingival plaque of the patients is removed using an ultrasound probe, the teeth are isolated with balls of cotton wool and the treated sites are rinsed with water and delicately dried by air jet. The treated site is then filled with the active suspension with the aid of a syringe onto which has been placed a foam-tipped needle.

For the measurements of the rate of diffusion of the benzoic acid and of the metronidazole, samples of gingival fluid are collected at various periods of time after filling of the site, with the aid of 2×13-mm strips of Whatmann paper No. 4 which are introduced into the crevical part of the pocket to a depth of 1 to 2 mm and kept in this position for 120 seconds in order to allow the absorption of the fluid. The filter papers are conserved at −10° C. in sterile polypropylene tubes.

The amounts of metronidazole benzoate in the gingival fluid were determined by HPLC (Waters™ machine using a Waters™ 486 UV detector, a 5 $\mu$m C18 Chomospher™ column and, as the mobile phase, a 40/60 vol/vol mixture of water (buffered with potassium nitrate and sodium acetate, whose pH has been adjusted to 5.5 by means of acetic acid) and of methanol; flow rate 1 ml/min).

The results of the assays, which are expressed as $\mu$g of metronidazole per ml of crevicular fluid as a function of time, are given in Table 14.

TABLE 14

Preparation $A_2$:
Mean concentrations, expressed as metronidazole, as a function of time

| Time (h) | Mean concentration ($\mu$g/ml) | Standard error of the mean |
|---|---|---|
| 0.5 | 177.03 | 56.0 |
| 5.5 | 13.48 | 2.2 |
| 9.5 | 3.35 | 1.1 |
| 25 | 16.38 | 1.1 |
| 50 | 16.67 | 1.9 |
| 85 | 18.39 | 1.3 |
| 135 | 14.07 | 0.8 |
| 200 | 14.29 | 0.8 |

The results obtained show that the calculated metronidazole concentration in the crevicular fluid is, for a period greater than 8 days, very much higher than the minimum inhibitory concentration (MIC) for metronidazole-sensitive anaerobic pathogenic micro-organisms of 1.75 to 5 $\mu$g/ml Elysol™, which is a metronidazole benzoate preparation containing a 25% dose of metronidazole, itself gives, according to K. Stolze (J. Clin. Periodontol., 19, 698–701 (1992)), concentrations in the crevicular fluid which are given in Table 15.

TABLE 15

Elysol:
Mean concentrations expressed as a function of time

| Time (h) | Mean concentration ($\mu$g/ml) | Standard error of the mean |
|---|---|---|
| 12 | 30.0 | 7.6 |
| 24 | 8.5 | 5.4 |
| 36 | 1.3 | 1.0 |

After 36 hours, the concentration expressed as metronidazole is lower than the MIC.

What is claimed is:

1. A method for treating a person or an animal suffering from periodontitis which comprises applying into one or more periodontal pockets a fluid pharmaceutical composition which allows the controlled release of at least one active substance and which comprises a) a therapeutically effective amount of at least one active substance,
   b) from 3 to 55% by weight of phospholipid,
   c) from 16 to 72% by weight of pharmaceutically acceptable solvent, and
   d) from 4 to 52% by weight of fatty acid, said composition having the property of gelling instantaneously in the presence of an aqueous phase.

2. The method composition according to claim 1, wherein the active substance is chosen from antibiotics, anti-infectious agents, local anesthetics, anti-inflammatory agents, anti-mycotic agents and peptide active substances.

3. The method according to claim 1, wherein the phospholipid is chosen from phosphatidylcholine, phosphatidylglycerol salts, dicaproylphosphatidylcholine and distearoylphosphatidylglycerol salts, alone or as a mixture.

4. The method according to claim 3, wherein the pharmaceutical composition contains from 15 to 55% by weight of phospholipid.

5. The method according to claim 1, wherein the phospholipid is a hydrogenated phosphatidylcholine.

6. The method according to claim 5, wherein the composition contains from 3 to 11% by weight of phospholipid.

7. The method according to claim 1, wherein the pharmaceutically acceptable solvent is chosen from propylene glycol, polyethylene glycols and mineral oils, alone or as a mixture.

8. The method according to claim 1, wherein the fatty acids present in said composition are saturated or unsaturated organic carboxylic acids containing from 4 to 22 carbon atoms.

9. The method according to claim 8, wherein the fatty acids are chosen from oleic acid, caprylic acid, capric acid, caproic acid, myristic acid and butyric acid, alone or as a mixture.

10. The method according to claim 1, wherein the composition also comprises up to 5% by weight of monoglyceride or of diglyceride or of a mixture of mono- and of diglyceride, and/or up to 15% by weight of triglycerides.

11. The method according to claim 3, wherein the pharmaceutical composition contains from 15 to 51% by weight of phospholipid.

12. The method according to claim 5, wherein the composition contains from 3 to 10% by weight of phospholipid.

13. The method according to claim 1, wherein the fatty acids present in said composition are saturated or unsaturated organic carboxylic acids containing from 8 to 18 carbon atoms.

14. The method according to claim 7, wherein the mineral oils are selected from the group consisting of liquid paraffin and silicone oils.

* * * * *